United States Patent [19]

Metcalf et al.

[11] 4,183,858
[45] Jan. 15, 1980

[54] α-VINYL TRYPTOPHANES

[75] Inventors: Brian W. Metcalf, Strasbourg; Michel Jung, Illkirch Graffenstaden, both of France

[73] Assignee: Merrell Toraude et Compagnie, Strasbourg, France

[21] Appl. No.: 812,113

[22] Filed: Jul. 1, 1977

[51] Int. Cl.² .............. C07D 209/20; A61K 31/405
[52] U.S. Cl. ....................... 260/326.14 T; 424/274
[58] Field of Search .............. 260/326.14 A, 326.14 T

[56] References Cited

U.S. PATENT DOCUMENTS 3,079,375  2/1963  Monroe et al. ............... 252/143
4,041,071  8/1977  Metcalf et al. ............... 260/293.86

FOREIGN PATENT DOCUMENTS 557705  5/1958  Canada .......................... 260/326.14 T

OTHER PUBLICATIONS

Metclaf et al. "Tetrahedron Letters," 41, pp. 3689–3692, (1977).
Mavcotte et al. "Biochemistry," 15, (1976), pp. 3070–3076.

Primary Examiner—Donald G. Daus
Assistant Examiner—D. B. Springer
Attorney, Agent, or Firm—L. Ruth Hattan; Eugene O. Retter; George W. Rauchfuss, Jr.

[57] ABSTRACT

Novel compounds of the following general formula

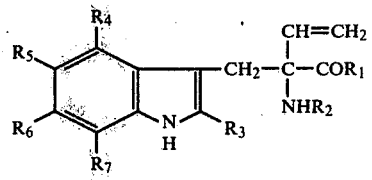

and pharmaceutically acceptable salts and individual optical isomers thereof. The compounds are useful as aromatic amine decarboxylase inhibitors.

8 Claims, No Drawings

α-VINYL TRYPTOPHANES

FIELD OF INVENTION

This invention relates to novel pharmaceutically useful α-vinyl amino acid derivatives which are inhibitors of aromatic amino acid decarboxylase.

BACKGROUND OF INVENTION

The amino acids tryptophan, 5-hydroxytryptophan, 3,4-dihydroxyphenylalanine (DOPA), tyrosine and phenylalanine are metabolically converted to tryptamine, 5-hydroxytryptamine, 3,4-dihydroxyphenethylamine or dopamine, tyramine and phenethylamino respectively by an aromatic amino acid decarboxylase. It is believed that the aromatic amino acid decarboxylase enzyme is non-specific, particularly, insofar as peripheral catalysis is concerned. Evidence does exist, however, to indicate that in the brain specific decarboxylation enzymes exist for each of DOPA and 5-hydroxytryptamine.

The above-enumerated aromatic amines are known to be involved in various pathophysiological processes. For example, it has been found that tryptamine, the decarboxylation product of tryptophan is enzymatically methylated to monomethyltryptamine which in turn is methylated enzymatically to dimethyltryptamine (DMT) in human red blood cells, plasma and platelets. The methylating enzyme is present in many mammalian species and has been shown to be produced in brain tissues of several species including man. DMT which has strong hallucinogenic or psychomimetic properties may play a role in the etiology of schizophrenia and other pyschotic disorders. Hence any agent which would block formation of DMT may be useful as an antipsychotic agent. Blocking the decarboxylation of tryptophan results in decreased levels of tryptamine, removing the substrate for DMT formation. Hence an inhibitor of aromatic amino acid decarboxylase which would block conversion of tryptophan to tryptamine may be useful as an antipsychotic agent.

Both 5-hydroxytryptamine (5-HT), the decarboxylation product of 5-hydroxytryptophan and 3,4-dihydroxyphenethylamine (dopamine) the decarboxylation product of DOPA are involved in peripheral and central physiological processes, and agents which are effective in the control of levels of these amines have resulted in useful pharmacological agents. It has been shown that central or brain levels of 5-HT and norepinephrine, which is formed metabolically by hydroxylation of dopamine, are higher in patients with manic disorders than in individuals without such disorders. It has also been shown that agents which decrease central levels of monoamines, for example, 5-HT and particularly norepinephrine have antimanic properties when given to human subjects, whereas drugs that increase monoamine levels could precipitate mania in susceptible individuals. Hence, agents which block formation of 5-HT and dopamine, such as, for example, by inhibiting the aromatic amino acid decarboxylation enzyme which converts 5-hydroxytryptophan and DOPA to 5-HT and dopamine respectively may be useful as antipsychotic agents or major tranquilizers in treating manic disorders.

It has also been shown that agents useful in inhibiting the decarboxylation of DOPA to dopamine are useful in the treatment of Parkinsonism when administered concurrently with exogenous DOPA or L-DOPA. It is believed that Parkinsonism is due, at least in part, to decreased central levels of dopamine since exogenous administration of DOPA or L-DOPA is known to be an effective means of treating Parkinsonism. However, since exogenously administered DOPA is readily converted enzymatically to dopamine peripherally it is necessary to administer large amounts in order to have increased absorption centrally. DOPA readily penetrates the blood-brain barrier whereas dopamine does not. Administration of DOPA or L-DOPA in conjunction with a peripherally active inhibitor of the enzyme which converts DOPA to dopamine reduces the amount of L-DOPA that must be administered in order to have adequate circulating levels for central absorption. Other advantages are also realized by administration of an aromatic amino acid decarboxylase inhibitor along with L-DOPA. By preventing formation of dopamine peripherally, side effects attributed to dopamine such as, cardiac arrhythmia, nausea and vomiting may be avoided.

Studies indicate that levels of 5-hydroxytryptamine (5-HT) are lower in patients with depressive syndromes than in individuals without such syndromes. Also, administration of exogenous L-5-hydroxytryptophan (L-5-HTP) is effective in treating certain depressed patients. However, as with DOPA, since L-5-HTP is readily metabolized peripherally to 5-HT in order to achieve increased central levels of the amino acid. It has been shown that by administering an inhibitor of the aromatic amino acid decarboxylase enzyme that catalyzes the formation of 5-HT from 5-HT peripherally the amount of exogenous 5-HTP required to give increased central levels is markedly reduced. In other words inhibitors of aromatic amino acid decarboxylase when used in conjunction with exogenous 5-HTP have been shown to be useful in treating depression.

Agents which block peripheral conversion of 5-HTP to 5-HT may be useful in treating other conditions which respond to increased central levels of 5-HTP as a result of exogenous administration of 5-HTP. It has been shown that exogenous L-5-HTP is useful in treating action myoclonus. Also, studies reveal that administration of exogenous 5-HTP is useful in treating insomnia. Hence concurrent administration of 5-HTP and an aromatic amino acid decarboxylase inhibitor may be beneficial in treating these conditions.

Blocking peripheral formation of 5-hydroxytryptamine may result in other beneficial effects since it is known that 5-HT is involved, for example, in the etiology of rheumatoid arthritis and the carbinoid syndrome by increasing collagen levels. Also, it is reported that 5-HT is the primary autocoid responsible for anaphylactoid reactions in human subjects as well as bronchoconstriction in asthmatic human subjects, and agents which antagonize or inhibit formation of 5-HT are useful in treating these conditions. 5-HT is known to cause platelet aggregation and has been implicated as a causal factor in the post-gastrectomy dumping syndrome and migraine headache. Methylsergide, a 5-hydroxytryptamine antagonist, has proven effective in treating post-gastrectomy dumping syndrome.

It has been suggested that phenethylamine, the decarboxylation product of phenylalanine, as an endogenous compound contributes to schizophrenic symptoms and triggers migraine headaches. Also, it has been suggested that endogenous tyramine, the decarboxylation product of tyrosine, contributes to seizure disorders.

Hence, it is readily evident that agents which are useful in regulating the levels of aromatic amino acids and amines find use in many pharmacological situations. The compounds of the present invention are inhibitors of the aromatic amino acid decarboxylase which converts tryptophan, 5-hydroxytryptophan, 3,4-dihydroxyphenylalanine, tyrosine and phenylalanine to the respective amines and hence provide useful pharmacologic agents.

SUMMARY OF INVENTION

The compounds of the present invention are represented by the following general Formula I:

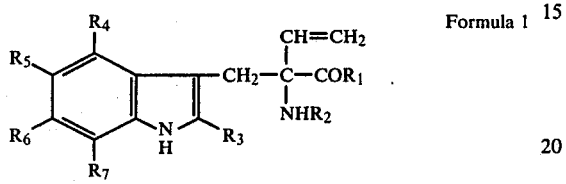

Formula 1 wherein $R_1$ is hydroxy, a straight or branched alkoxy group of from 1 to 8 carbon atoms, —NYY' wherein each of Y and Y' is hydrogen or a straight or branched lower alkyl group of from 1 to 4 carbon atoms or

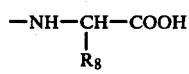

wherein $R_8$ is hydrogen, a straight or branched lower alkyl group of from 1 to 4 carbon atoms, benzyl or p-hydroxybenzyl; $R_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

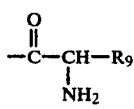

wherein $R_9$ is hydrogen, a straight or branched lower alkyl group of from 1 to 4 carbon atoms, benzyl or p-hydroxybenzyl; $R_3$ is hydrogen or methyl; $R_4$, $R_5$, $R_6$ and $R_7$ have the meanings defined in the following Table I wherein $R_{10}$ is hydrogen, a straight or branched alkyl group of from 1 to 8 carbon atoms, alkylcarbonyl wherein the alkyl moiety has from 1 to 6 carbon atoms and is straight or branched, benzoyl, or or phenylalkylenecarbonyl wherein the alkylene moiety has from 1 to 6 carbon atoms and is straight or branched, and halo is chlorine, fluorine, bromine or iodine:

TABLE I

| $R_4$ | $R_5$ | $R_6$ | $R_7$ |
|---|---|---|---|
| H | H | H | H |
| H | $OR_{10}$ | $OR_{10}$ | H |
| $OR_{10}$ | H | H | H |
| H | $OR_{10}$ | H | H |
| $OR_{10}$ | H | $OR_{10}$ | H |
| H | H | $OR_{10}$ | H |
| $OR_{10}$ | $OR_{10}$ | H | H |
| $CF_3$ | H | H | H |
| H | H | $CF_3$ | H |
| H | halo | H | H |
| H | H | halo | H |
| H | halo | halo | H |

TABLE I-continued

| $R_4$ | $R_5$ | $R_6$ | $R_7$ |
|---|---|---|---|
| halo | H | H | $CH_3$ |
| $OR_{10}$ | H | H | $CH_3$ |
| H | $OR_{10}$ | H | $CH_3$ |
| H | H | $OR_{10}$ | $CH_3$ |
| H | H | H | halo |
| H | halo | H | halo |
| H | H | halo | halo |
| halo | H | H | halo |
| H | H | $OR_{10}$ | halo |
| H | $OR_{10}$ | H | halo |
| $OR_{10}$ | H | H | halo |
| H | H | H | $CF_3$ |
| H | $OR_{10}$ | H | $CF_3$ |
| H | H | halo | $OR_{10}$ |
| H | $OR_{10}$ | H | $OR_{10}$ |
| H | halo | H | $OR_{10}$ |
| $OR_{10}$ | H | H | $OR_{10}$ |
| halo | H | H | $OR_{10}$ |

The pharmaceutically acceptable salts and individual optical isomers of the compounds of general Formula I are also included within the scope of this invention.

The compounds of general Formula I are useful pharmacological agents in that said compounds are inhibitors of aromatic amino acid decarboxylase and useful as intermediates in the preparation of useful pharmacological agents.

DETAILED DESCRIPTION OF INVENTION

In the compounds of general Formula I the term alkylcarbonyl is taken to mean a group of the structure

wherein the alkyl moiety has from 1 to 6 carbon atoms and can be a straight chain or a branched chain. Illustrative examples of the alkyl moiety in the substituent alkylcarbonyl group are methyl, ethyl, n-propyl, isopropyl, n-butyl, sec-butyl, tert-butyl, n-pentyl, neo-pentyl, tert-pentyl and hexyl.

The term benzoyl as used in reference to the compounds of general Formula I is taken to mean the group

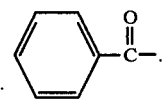

The term phenylalkylenecarbonyl as used in reference to the compounds of general Formula I is taken to mean a substituent group of the structure

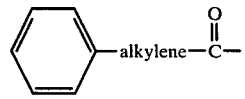

wherein the alkylene moiety has from 1 to 6 carbon atoms and can be a straight chain or a branched chain. Illustrative examples of the alkylene moiety in the substituent phenylalkylenecarbonyl group are methylene, ethylene, n-propylene, n-butylene, n-pentylene, hexylene, isopropylene, sec-butylene, tert-butylene and neopentylene.

Illustrative examples of straight or branched alkoxy groups of from 1 to 8 carbon atoms in the above general Formula I are methoxy, ethoxy, n-propoxy, n-butoxy, isopropoxy, tert-butoxy, pentoxy and octyloxy.

Illustrative examples of straight chain or branched chain lower alkyl groups of from 1 to 8 carbon atoms in the above general Formula I are methyl, ethyl, n-propyl, iso-propyl, n-butyl, tert-butyl, n-pentyl, hexyl, heptyl and octyl.

As used in general formula I the term alkoxycarbonyl is taken to mean the group

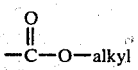

wherein the alkoxy group, that is, —O—alkyl has from 1 to 4 carbon atoms and is straight or branched, for example, methoxy, ethoxy, n-propoxy, isopropoxy, n-butoxy and tert-butoxy.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric, ascorbic and cyclamic acids; and non-toxic salts formed with inorganic or organic bases such as those of alkali metals, for example, sodium potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperazine. The salts are prepared by conventional means.

Preferred compounds of this invention are those of general Formula I wherein $R_2$ is hydrogen or alkylcarbonyl wherein the alkyl moiety has from 1 to 4 carbon atoms and is straight or branched, and of these preferred compounds a more preferred group are those wherein $R_1$ is hydroxy or a straight or branched alkoxy group of from 1 to 8 carbon atoms. Another preferred embodiment of this invention is compounds of general Formula I wherein each of $R_4$, $R_5$, $R_6$ or $R_7$ is hydrogen or $OR_{10}$ wherein $R_{10}$ is hydrogen. The most preferred compounds of this invention are those of general Formula I wherein $R_5$ is hydrogen or hydroxy, $R_1$ is hydroxy and $R_2$ is hydrogen.

Illustrative examples of compounds of the present invention are the following:

2-amino-3-(3-indolyl)-2-vinylpropionic acid,
2-amino-3-[3-(5-hydroxy)indolyl]-2-vinylpropionic acid,
2-amino-3-[3-(5-(1-oxoethoxy))indolyl]-2-vinylpropionic acid,
2-amino-3-[3-(5-(1-oxo-n-butoxy))indolyl]-2-vinylpropionic acid,
2-amino-3-[3-(6-methoxy)indolyl]-2-vinylpropionic acid,
2-amino-3-[3-(5-ethoxy)indolyl]-2-vinylpropionic acid,
2-amino-3-[3-(5-benzoyloxy)indolyl]-2-vinylpropionic acid,
2-amino-3-[3-(5-(1-oxo-2-phenylethoxy))indolyl]-2-vinylpropionic acid,
2-amino-3-[3-(6-(1-oxo-2-phenyl-n-butoxy))indolyl]-2-vinylpropionic acid,
methyl 2-amino-3-(3-indolyl)-2-vinylpropionate,
ethyl 2-amino-3-[3-(5-hydroxy)indolyl]-2-vinylpropionate,
n-propyl 2-amino-3-[3-(5-(1-oxoethoxy))indolyl]-2-vinylpropionate,
n-butyl 2-amino-3-[3-(5-(1-oxo-n-butoxy))indolyl]-2-vinylpropionate,
isopropyl 2-amino-3-[3-(6-methoxy)indolyl]-2-vinylpropionate,
tert-butyl 2-amino-3-[3-(5-ethoxy)indolyl]-2-vinylpropionate,
n-pentyl 2-amino-3-[3-(5-benzoyloxy)indolyl]-2-vinylpropionate,
isopentyl 2-amino-3-[3-(5-(1-oxo-2-phenylethoxy))indolyl]-2-vinylpropionate,
tert-pentyl 2-amino-3-[3-(6-(1-oxo-2-phenyl-n-butoxy))indolyl]-2-vinylpropionate,
ethyl 2-amino-3-[3-(6-hexyloxy)indolyl]-2-vinylpropionate,
2-amino-3-(3-indolyl)-2-vinylpropionamide,
N,N-diethyl 2-amino-3-[3-(5-hydroxy)indolyl]-2-vinylpropionamide,
N-n-propyl 2-amino-3-[3-(5-(1-oxoethoxy))indolyl]-2-vinylpropionamide,
N-n-butyl 2-amino-3-[3-(5-(1-oxo-n-butoxy))indolyl]-2-vinylpropionamide,
N-methyl 2-amino-3-[3-(6-methoxy)indolyl]-2-vinylpropionamide,
N-ethyl 2-amino-3-[3-(5-ethoxy)indolyl]-2-vinylpropionamide,
N,N-dimethyl 2-amino-3-[3-(5-benzoyloxy)indolyl]-2-propionamide,
N-tert-butyl 2-amino-3-[3-(5-(1-oxo-2-phenylethoxy))indolyl]-2-vinylpropionamide,
N-methyl 2-amino-3-[3-(5-benzoyloxy)indolyl]-2-vinylpropionamide,
N-n-butyl 2-amino-3-[3-(5-(1-oxo-2-phenylethoxy))indolyl]-2-vinylpropionamide,
2-[2-amino-3-(3-indolyl)-1-oxo-2-vinylpropylamino]acetic acid,
2-[2-amino-3-[3-(5-hydroxy)indolyl]-1-oxo-2-vinylpropylamino]acetic acid,
2-[2-amino-3-[3-(5-(1-oxoethoxy))indolyl]-1-oxo-2-vinylpropylamino]propionic acid,
2-[2-amino-3-[3-(5-(1-oxo-n-butoxy))indolyl]-1-oxo-2-vinylpropylamino]-2-benzylacetic acid,
2-(1-oxoethylamino)-3-[3-(6-methoxy)indolyl]-2-vinylpropionic acid,
2-(N-ethoxycarbonylamino)-3-[3-(5-ethoxy)indolyl]-2-vinylpropionic acid,
2-[N-(2-amino-1-oxoethyl)amino]-3-[3-(5-(1-oxo-2-phenylethoxy))indolyl]-2-vinylpropionic acid,
2-[2-amino-3-[3-(6-(1-oxo-2-phenyl-n-butoxy))indolyl]-1-oxo-2-vinylpropylamino]butyric acid,
2-[N-(2-amino-1-oxo-3-phenylpropyl)amino]-3-[3-(5-hexyloxy)indolyl]-2-vinylpropionic acid,
2-[2-(1-oxoethylamino)-3-(3-indolyl)-1-oxo-2-vinylpropylamino]acetic acid,
methyl 2-(1-oxobutylamino)-3-(3-(5-hydroxy)indolyl)-2-vinylpropionate,
2-[2-(N-ethoxycarbonylamino)-3-(3-(5-hydroxy)indolyl]-2-vinylpropionic acid,
N-methyl 2-(1-oxoethylamino)-3-(3-(5-hydroxy)indolyl)-2-vinylpropionamide,
2-amino-3-[3-(3-methyl)-indolyl]-2-vinylpropionic acid,
2-amino-3-[3-(5-hydroxy-3-methyl)indolyl]-2-vinylpropionic acid, 2-amino-3-[3-(4-hydroxy)indolyl]-2-vinylpropionic acid,
2-amino-3-[3-(6-trifluoromethyl)indolyl]-2-vinylpropionic acid,
2-amino-3-[3-(5-fluoro)indolyl]-2-vinylpropionic acid,
2-amino-3-[3-(5,6-dichloro-3-methyl)-indolyl]-2-vinylpropionic acid,
2-amino-3-[3-(4-bromo-7-methyl)indolyl]-2-vinylpropionic acid,
2-amino-3-[3-(7-chloro-6-hydroxy-3-methyl)indolyl]-2-vinylpropionic acid,
2-amino-3-[3-(5-hydroxy-7-trifluoromethyl)indolyl]-2-vinylpropionic acid, and
2-amino-3-[3-(4-fluoro-7-methoxy-3-methyl)indolyl]-2-vinylpropionic acid.

The compounds of general Formula I are irreversible inhibitors of the enzyme which metabolically catalyzes the conversion of tryptophan, 5-hydroxytryptophan, 3,4-dihydroxyphenylalanine, tyrosine and phenylanine to tryptamine, 5-hydroxytryptamine, 3,4-dihydroxyphenylethylamine, tyramine and phenethylamine respectively. As indicated hereinabove results of studies indicate that the enzyme responsible for the conversion of the above-enumerated amino acids to the respective amines peripherally is a non-specific aromatic amino acid decarboxylase. For central conversion studies indicate that specific decarboxylases are responsible for the conversion of each of 5-hydroxytryptophan and 3,4-dihydroxyphenylalanine whereas the remaining above-enumerated amino acids are enzymatically transformed to the respective amines by a non-specific aromatic decarboxylase. The compounds of the present invention are effective in irreversibly inhibiting both centrally and peripherally the activity of non-specific aromatic amino acid decarboxylase as well as the activity of 5-hydroxytryptophan (5-HTP) decarboxylase. As used herein with regard to the utility of the compounds of the present invention the term central refers to the central nervous system, primarily the brain, whereas peripheral refers to other body tissues wherein the decarboxylase enzyme is present. Selectivity of inhibition of the amino acid decarboxylases centrally or peripherally by administering compounds of general Formula I is dose dependent.

As irreversible inhibitors of aromatic amino acid decarboxylase and 5-HTP decarboxylase the compounds of the present invention possess many pharmacological utilities. As peripheral irreversible inhibitors of aromatic amino acid decarboxylase the compounds of general Formula I are useful in the treatment of Parkinsonism when given in conjunction with 3,4-dihydroxyphenylalanine (DOPA) or L-3,4-dihydroxyphenylalanine (L-DOPA). DOPA and more particularly the active isomer L-DOPA are known to be effective in treating Parkinsonism when administered systemically, usually in an amount from 0.5 to 1 gram daily initially after which the amount administered is gradually increased over a 3 to 7 day period to a maximally tolerated daily dose of about 8 grams. Concurrent administration of a compound of general Formula I and L-DOPA provides an improved method of treating Parkinsonism in that the compounds of Formula I will block the decarboxylation of L-DOPA to L-3,4-dihydroxyphenethylamine (L-dopamine) peripherally by inhibiting the activity of aromatic amino acid decarboxylase enzyme, thus retaining high circulating levels of L-DOPA for central absorption and also preventing peripheral formation of increased levels of dopamine which is known to result in certain undesirable side effects such as cardiac arrhythmias. By concurrently administering a compound of general Formula I and L-DOPA the amount of L-DOPA administered may be reduced 2 to 10-fold as compared to amounts required for utility when L-DOPA is administered alone. It is preferred that the compounds of this invention be administered prior to the administration of L-DOPA. For example, a compound of Formula I may be administered from 30 minutes to 4 hours prior to administration of L-DOPA depending on the route of administration and condition of the patient to be treated.

The compounds of general Formula I are also useful in treating depressive syndromes in individuals when given in conjunction with 5-hydroxytryptophan (5-HTP) or more particularly the active levo isomer which is known to be useful in the treatment of depression when administered systemically. The compounds of general Formula I, by inhibiting peripherally the activity of aromatic amino acid decarboxylase will block the conversion of 5-hydroxytryptophan to 5-hydroxytryptamine thus retaining higher circulating levels of 5-HTP for central absorption. The compounds of general Formula I when administered concurrently with exogenous 5-HTP are also useful in treating action myoclonus which is known to be effectively treated by increasing central levels of 5-HTP.

The compounds of general Formula I, by virtue of their inhibitory action on aromatic amino acid decarboxylase peripherally are also useful in the treatment of rheumatoid arthritis, carcinoid syndrome, anaphylactoid reactions in humans, bronchoconstriction in asthmatic humans as well as other conditions known to be caused by high peripheral levels of 5-hydroxytryptamine.

As indicated hereinabove it has been shown that agents which decrease the elevated levels of 5-HT and norepinephrine, the hydroxylation product of dopamine, are useful in treating patients with manic disorders. Hence, as central irreversible inhibitors of aromatic amino acid decarboxylase and 5-HTP decarboxylase the compounds of general Formula I are useful in treating manic disorders. Additionally by virtue of the central inhibitory action of the compounds of general Formula I on aromatic amino acid decarboxylase said compounds may also be useful as antipsychotic agents, since central levels of tryptamine are decreased, and useful in treatment of schizophrenia and seizure disorders since central levels of phenethylamine and tyramine are decreased by administration of a compound of general Formula I.

The utility of the compounds of general Formula I as irreversible inhibitors of aromatic amino acid decarboxylase may be demonstrated as follows. A compound of general Formula I is administered as an aqueous solution or suspension to rats or mice. At different time intervals after administration of the compound from 1 to 48 hours the animals are sacrificed by decapitation and aromatic amino acid decarboxylase activity is measured by a radiometric assay as described by Christenson et al., Arch. Biochem. Biophys. 141, 356 (1970) in homogenates of kidney, heart and brain prepared according to Burkard et al., Arch. Biochem. Biophys. 107, 187 (1964).

The compounds of this invention can be administered in various manners to achieve the desired effect. The compounds can be administered alone or in the form of pharmaceutical preparations to the patient being treated either orally, parenterally, that is, subcutaneously, intravenously or intraperitoneally, or topically. The compounds can be administered by intranasal instillation or by application to mucous membranes such as that of the nose, throat and bronchial tubes, for example, in an aerosol spray containing small particles of a novel compound of this invention in a spray solution or dry powder form.

The amount of novel compound administered will vary and can be any effective amount. Depending on the patient, the condition being treated and the mode of administration, the quantity of novel compound administered may vary over a wide range to provide an effective amount in a unit dosage form. When the compounds of general Formula I are administered to affect a peripheral irreversible inhibition of aromatic amino acid decarboxylase the effective amount of compound administered will vary from 0.1 mg/kg (milligrams per kilogram) to 100 mg/kg of body weight of the patient per dose and preferably from about 5 to 25 mg/kg to achieve the desired effect. For example, the desired effect can be obtained by consumption of a unit dosage form, such as, for example, a tablet containing from 10 to 250 mg of a novel compound of this invention taken 1 to 4 times daily. When the compounds of general Formula I are administered to achieve a central irreversible inhibition of aromatic decarboxylase or 5-hydroxytryptophan decarboxylase the effective amount of compound administered will vary from about 100 mg/kg to 500 mg/kg of body weight of the patient per day and preferably from about 150 mg/kg to 300 mg/kg. For example, the desired central effect can be achieved by consumption of a unit dosage form, such as, for example, a tablet containing from about 350 mg to 500 mg of a novel compound of this invention taken from 1 to 4 times daily.

As used herein the term patient is taken to mean warm blooded animals such as mammals, for example, cats, dogs, rats, mice, guinea pigs, sheep, horses, bovine cows, and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petrolem, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

For use as aerosols the novel compounds in solution or suspension may be packaged in a pressurized aerosol container together with a gaseous or liquified propellant, for example, dichlorodifluoromethane, dichlorodifluoromethane with dichlorodifluoroethane, carbon dioxide, nitrogen or propane, with the usual adjuvants such as cosolvents, and wetting agents, as may be necessary or desirable. The compounds may also be administered in a non-pressurized form such as in a nebulizer or atomizer.

As indicated hereinabove the compounds of general Formula I find particular utility when administered together with exogenous L-DOPA in which case individual formulations of a compound of general Formula I and L-DOPA may be administered, or both active ingredients may be formulated into a single combination pharmaceutical formulation. In either mode of administration the amount of compound of general Formula I as compared to the amount of L-DOPA administered will vary from about 1:1 to 1:10. A combination formulation may contain an internal portion containing L-DOPA and an outer portion containing a compound of general Formula I, each active ingredient being suitably formulated. A particularly suitable combination formulation may be prepared by compressing L-DOPA, optionally with suitable carriers, to a core, providing said core with a laminated coating that is resistant to gastric juice, and applying over the coated core an external layer that contains a compound of general Formula I suitably formulated. Using such a combination formulation the decarboxylase inhibitor, that is, a compound of general Formula I is released, preferably 30 to 60 minutes prior to the L-DOPA. The laminated coating may be formed by use of a nonaqueous solution of glycerides or a water-insoluble polymer such as ethyl cellulose or cellulose acetate phthalate. A formulation wherein the L-DOPA is enteric coated by use of mixtures of shellacs and shellac derivatives and cellulose acetate phthalates may also be employed.

In the specific examples included hereinbelow illustrative examples of suitable pharmaceutical formulations are described.

In addition to being useful pharmacological agents, the compounds of this invention wherein $R_1$ is hydroxy are useful as intermediates for the preparation of cephalosporin derivatives which are useful as antibiotics. The compounds of general Formula I wherein $R_1$ is hydroxy are useful in the preparation of cephalosporin derivatives of the following general Formula II.

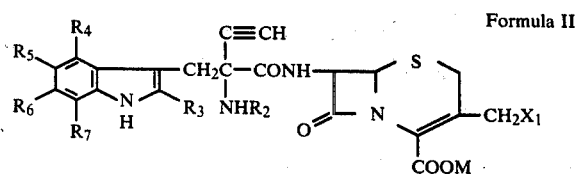

Formula II

In the above general Formula II, $X_1$ is hydrogen or acetoxy; M is hydrogen or a negative charge; and $R_2$, $R_3$, $R_4$, $R_5$, $R_6$ and $R_7$ have the meanings defined in general Formula I.

The compounds of general Formula II and the pharmaceutically acceptable salts and individual optical isomers thereof are novel compounds useful as antibiotics and can be administered in a manner similar to that of many well known caphalosporin derivatives, for example, cephalexin, cephalothin, or cephaloglycine. The compounds of general Formula II and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula II, salts and isomers thereof may be incorporated into creams or ointments.

Illustrative examples of bacteria against which the compounds of general Formula II and the pharmaceutically acceptable salts and individual optical isomers thereof are active are *Staphylococcus aureus, Salmonella schottmuelleri, Klebsiella pneumoniae, Diplococcus pneumoniae* and *Streptococcus pyogenes.*

Illustrative pharmaceutically acceptable non-toxic inorganic acid addition salts of the compounds of general Formula II are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of cephalosporin derivatives as represented by general Formula II are 7-[[2-amino-3-(3'-indolyl)-2-vinylpropionyl]amino]-3-acetyloxymethyl-8-oxo-5-thia-1-azabicyclo[4.2.0]oct-2-ene-2-carboxylic acid, 7-[[2-amino-3-(3'-(5'-hydroxy)indolyl)-2-vinylpropionyl]amino]-3-acetyloxymethyl-8-oxo-5-thia-1-azabicyclo[4.2.0]oct-2-ene-2-carboxylic acid and 7-[[2-amino-3-(3'-(5'-(1-oxoethoxy))indolyl)-2-vinylpropionyl]amino]-3-acetyloxymethyl-8-oxo-5-thia-1-azabicyclo[4.2.0]oct-2-ene-2-carboxylic acid.

The preparation of the compounds of general Formula II is described hereinbelow.

The compounds of general Formula I wherein $R_1$ is hydroxy, $R_2$ is hydrogen, $R_3$ is hydrogen or methyl and each of $R_4$, $R_5$, $R_6$ and $R_7$ is hydrogen or $OR_{10}$ wherein $R_{10}$ is hydrogen or a straight or branched alkyl group of from 1 to 8 carbon atoms are prepared by slowly adding one equivalent of a mineral salt of a phenylhydrazine derivative of the formula

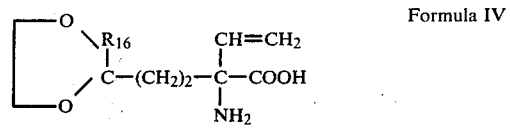

Formula III in an appropriate solvent and a catalytic amount of a mineral acid, such as hydrochloric acid, or an organic acid, such as, acetic acid or formic acid to one equivalent of an acetal of the formula

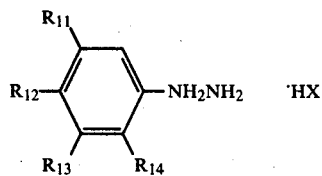

Formula IV wherein $R_{16}$ is hydrogen or methyl, in water, an aqueous lower alcohol or aqueous acetic or formic acid.

In the above general Formula III, X is halogen, for example, chlorine or bromine, each of $R_{11}$, $R_{12}$, $R_{13}$ and $R_{14}$ have the meanings defined in the following Table II wherein $R_{15}$ is a straight or branched alkyl group of from 1 to 8 carbon atoms, such as, methyl, ethyl, n-propyl, isopropyl, n-butyl, pentyl, hexyl, heptyl or octyl when in the compounds of Formula I $R_{10}$ is a straight or branched alkyl group of from 1 to 8 carbon atoms, or benzyloxy or 2,4-dimethoxybenzyloxy when in the compounds of Formula I $R_{10}$ is hydrogen, and halo is chlorine, fluorine, bromine or iodine:

TABLE II

| $R_{11}$ | $R_{12}$ | $R_{13}$ | $R_{14}$ |
|---|---|---|---|
| H | H | H | H |
| H | $OR_{15}$ | $OR_{15}$ | H |
| $OR_{15}$ | H | H | H |
| H | $OR_{15}$ | H | H |
| $OR_{15}$ | H | $OR_{15}$ | H |
| H | H | $OR_{15}$ | H |
| $OR_{15}$ | $OR_{15}$ | H | H |
| $CF_3$ | H | H | H |
| H | H | $CF_3$ | H |
| H | halo | H | H |
| H | H | halo | H |
| H | halo | halo | H |
| halo | H | H | $CH_3$ |
| $OR_{15}$ | H | H | $CH_3$ |
| H | $OR_{15}$ | H | $CH_3$ |
| H | H | $OR_{15}$ | $CH_3$ |
| H | H | H | halo |
| H | halo | H | halo |
| H | H | halo | halo |
| halo | H | H | halo |
| H | H | $OR_{15}$ | halo |
| H | $OR_{15}$ | H | halo |
| $OR_{15}$ | H | H | halo |
| H | H | H | $CF_3$ |
| H | $OR_{15}$ | H | $CF_3$ |
| H | H | halo | $OR_{15}$ |
| H | $OR_{15}$ | H | $OR_{15}$ |
| H | halo | H | $OR_{15}$ |
| $OR_{15}$ | H | H | $OR_{15}$ |
| halo | H | H | $OR_{15}$ |

The reaction mixture is heated to about 90° C. for about 4 hours then concentrated to dryness. The residue is dissolved in water, and the pH of the solution is adjusted to 6. The solution is applied to a column of Amberlite resin 120 H+. Elution with 1 molar ammonium hydroxide gives the above-described compounds of Formula I with the additional step of debenzylation with boron tribromide, boron trichloride or lithium-ammonia when $R_{15}$ is benzyloxy, or with trifluoroacetic acid when $R_{15}$ is 2,4-dimethoxybenzyloxy in the presence of a scavenger such as 1,3-dimethoxybenzene.

The compounds of general Formula I wherein $R_1$ is hydroxy, $R_2$ is hydrogen and $R_{10}$ is a straight or branched alkyl group of from 1 to 8 carbon atoms may also be prepared by alkylating the corresponding compound wherein $R_{10}$ is hydrogen with an alkyl halide of the formula $R_{17}X_2$ wherein $R_{17}$ is a straight or branched alkyl group of from 1 to 8 carbon atoms and $X_2$ is halogen, for example, bromine or iodine in a lower alcoholic solvent such as methanol or ethanol or hydrocarbon solvents such as benzene or toluene in the presence of an organic base such as triethylamine, pyridine or in an aprotic solvent such as dimethylformamide, dimethylacetamide or dimethylsulfoxide in the presence of sodium hydride for about 1 to 24 hours at a temperature of from about 25° C. to 85° C. followed by hydrolysis with aqueous base or acid with the proviso that prior to the alkylation reaction the α-amino group of the hydroxy substituted starting material is protected with a suitable protecting group such as tert-butoxycarbonyl which is subsequently removed by treatment with acid, for example, trifluoroacetic acid. The alky halides employed in the above reaction are known in the art or can be prepared by procedures well known in the art.

The compounds of general Formula I wherein $R_1$ is hydroxy or a straight or branched alkoxy group of from 1 to 8 carbon atoms, $R_2$ is hydrogen and $R_{10}$ is alkylcarbonyl wherein the alkyl moiety has from 1 to 6 carbon atoms and is straight or branched, benzoyl, or phenylalkylenecarbonyl wherein the alkylene moiety is straight or branched and has from 1 to 6 carbom atoms are prepared by treating the corresponding derivatives wherein $R_{10}$ is hydrogen with an acid anhydride of the formula

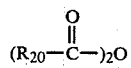

or an acid halide of the formula

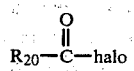

wherein halo is chlorine or bromine and $R_{20}$ is a straight or branched alkyl group of from 1 to 6 carbon atoms, phenyl or phenylalkylene wherein the alkylene moiety is straight or branched and has from 1 to 6 carbon atoms in the presence of an organic base such as pyridine, quinoline or triethylamine, which base serves as the solvent, for from about 1 to 24 hours at a temperature of from about 25° C. to 100° C. with the proviso that prior to the reaction the α-amino group of the starting material is protected with a suitable blocking group, such as, tert-butoxycarbonyl which is subsequently removed by treatment with acid, for example, trifluoroacetic acid.

The acid anhydride and acid halide reactants employed in the above reaction are known in the art or can be prepared from the appropriate acids by procedures well known in the art.

The compounds of general formula III are known in the art or can be prepared by methods known in the art, and HX represents a mineral acid, such as hydrochloric acid. The compounds of general Formula III which are not known in the art may be prepared from the appropriately substituted nitrobenzene derivatives which are known in the art. For example, the nitrobenzene derivative in a solvent such as, lower alcohols, for example methanol or ethers, such as tetrahydrofuran or diethyl ether, chloroform or acetic acid is treated with 5% palladium on charcoal or platinum catalyst under a hydrogen atmosphere and treating with a mineral acid such as hydrochloric acid to give the corresponding amine HCl derivative. The amine derivative is diazotized, for example, in concentrated hydrochloric acid using sodium nitrite, and the thus obtained diazonium salt is reduced with stannous chloride for from 2 to 18 hours at a temperature of from 0° to 5° C. to give the hydrazine derivative. The compounds of Formula III wherein $R_{15}$ is a straight or branched alkyl group of from 1 to 8 carbon atoms are obtained by treating the corresponding phenol acetamide in an alcoholic solvent such as a lower alcohol solvent, for example, ethanol, aprotic solvents such as dimethylformamide, dimethylacetamide or dimethyl sulfoxide in the presence of a base such as potassium carbonate, sodium hydride or a trialkylamine such as triethylamine with alkyl bromide for from 1 to 24 hours at a temperature of from 25° C. to 100° C. The thus obtained alkoxyphenylacetamide is hydrolyzed in an alcoholic solvent with a base such as potassium hydroxide or sodium hydroxide for from 4 to 18 hours at a temperature of from 60° C. to 90° C. to afford the corresponding free amine which is diazotized in concentrated hydrochloric acid using sodium nitrite. The diazonium salt thus obtained is reduced with stannous chloride for from 2 to 18 hours at a temperature of from 0° C. to 5° C. to obtain the desired alkoxyphenylhydrazine.

The compounds of general Formula IV are prepared from the corresponding acetylene derivatives, that is, 2-acetylene-2-amino-4-(1,3-dioxolan-2-yl)butyric acid and 2-acetylene-2-amino-4-(2-methyl-1,3-dioxolan-2-yl)butyric acid by chemical reduction. The reduction is achieved by treating the acetylene derivative in liquid ammonia containing ammonium sulfate with lithium, sodium or potassium metal until the blue color persists at a temperature of from −70° to 25° C.

The compounds of general Formula I wherein $R_1$ is a straight or branched alkoxy group of from 1 to 8 carbon atoms are prepared by treating the corresponding derivatives wherein $R_1$ is hydroxy with thionyl chloride to form the acid chloride which is reacted with an alcohol of the formula $R_{18}$—OH, wherein $R_{18}$ is a straight or branched alkyl group of from 1 to 8 carbon atoms, such as, methyl, ethyl, n-propyl, isopropyl, n-butyl, tert-butyl, hexyl, or octyl, at about 25° C. for from about 4 to 12 hours.

The compounds of general Formula I wherein $R_1$ is —NYY' wherein each of Y and Y' is hydrogen or a straight or branched lower alkyl of 1 to 4 carbon atoms are prepared by an acylation reaction of an acid halide, for example, an acid chloride, of the corresponding compound wherein $R_1$ is hydroxy and $R_2$ has the meaning defined in Formula I with the proviso that any free amino group is protected with a suitable protecting group, for example, carbobenzyloxy or tert-butyoxycarbonyl and when $R_{10}$ is hydrogen said group is protected as the corresponding alkylcarbonyloxy group, with an excess of an appropriate amine which may be represented as HYY'. The reaction is carried out in methylene chloride, chloroform, dimethylformamide, ethers such as tetrahydrofuran or dioxane or benzene at about 25° C. for about 1 to 4 hours. Suitable amines are, for example, ammonia, or a compound which is a potential source of ammonia, for example, hexamethylenetetramine; primary amines, for example, methylamine, ethylamine, or n-propylamine; and secondary amines such as dimethylamine, diethylamine or di-n-butylamine. Following the acylation reaction the α-amino protecting group is removed by treatment with acid or hydrogen bromide in dioxane, and the hydroxy protecting group when appropriate is removed by base hydrolysis.

The compounds of general Formula I wherein $R_1$ is

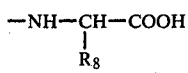

are prepared by reacting the corresponding derivative wherein $R_1$ is hydroxy or a functional derivative thereof such as an acid anhydride, $R_{10}$ is alkylcarbonyloxy and $R_2$ has the meaning defined in Formula I with the proviso that any free amine group is protected with a suitable blocking group, such as benzyloxycarbonyl, tert-butoxycarbonyl with a compound of the formula

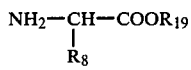

wherein $R_8$ has the meaning defined in general Formula I and $R_{19}$ is a lower alkyl group, for example, methyl or ethyl in an ether solution, such as tetrahydrofuran or dioxane at about 0° C. to 50° C. for 1 to 24 hours, with the proviso that when the free acid is employed the reaction is carried out using a dehydrating agent such as dicyclohexylcarbodiimide. The protecting groups are removed by acid hydrolysis with, for example, trifluoroacetic acid or hydrogen bromide in dioxane for about 1 to 20 hours.

The compounds of general Formula I wherein $R_2$ is alkylcarbonyl wherein the alkyl moiety is straight or branched and has from 1 to 4 carbon atoms are prepared by treating the corresponding derivatives wherein $R_2$ is hydrogen, and $R_1$ is hydroxy with an acid halide of the formula

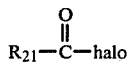

wherein halo is a halogen atom, for example, chlorine or bromine and $R_{21}$ is a straight or branched alkyl group having from 1 to 4 carbon atoms in water in the presence of a base such as sodium hydroxide or sodium borate at a temperature of from 0° C. to 25° C. for from ½ hour to 6 hours. These compounds may also be prepared from the ester derivative, that is, compounds of general Formula I wherein $R_2$ is hydrogen and $R_1$ is an alkoxy group of from 1 to 8 carbon atoms by treatment with the acid halide

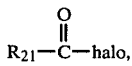

described above, in water, methylene chloride, chloroform or dimethyl acetamide in the presence of a base such as sodium hydroxide, potassium hydroxide or excess triethylamine at a temperature of from about 0° C. to 25° C. for from about ½ hour to 24 hours.

The compounds of general Formula I wherein $R_2$ is alkoxycarbonyl wherein the alkoxy moiety is straight or branched and has from 1 to 4 carbon atoms are prepared by treating the corresponding derivative wherein $R_2$ is hydrogen and $R_1$ is hydroxy with a halo alkylformate of the formula

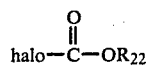

wherein halo is a halogen atom such as chlorine or bromine and $R_{22}$ is a straight or branched alkyl group having from 1 to 4 carbon atoms in water in the presence of a base such as sodium hydroxide or sodium borate at a temperature of from about 0° C. to 25° C. for from about ½ hour to 6 hours.

The compounds of general Formula I wherein $R_2$ is

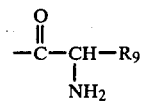

wherein $R_9$ is hydrogen, a straight or branched lower alkyl group of from 1 to 4 carbon atoms, benzyl or p-hydroxybenzyl are prepared by treating the corresponding derivative wherein $R_2$ is hydrogen and $R_1$ is a straight or branched alkoxy group of from 1 to 8 carbon atoms with an acid of the formula

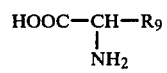

or an anhydride thereof wherein the amino group is protected with a suitable blocking group such as benzyloxycarbonyl or tert-butoxycarbonyl and $R_9$ has the meaning defined hereinabove in an ether, such as, tetrahydrofuran or dioxane, methylene chloride or chloroform and in the presence of a dehydrating agent when the free acid is employed, at a temperature of about 0° C. to 35° C. for about 1 to 12 hours followed by acid and base hydrolysis to remove the protecting groups.

The individual optical isomers of the compounds of general formula I wherein $R_2$ is H and $R_1$ is OH may be separated by using a (+) or (−) binahpthylphosphoric acid salt by the method of R. Viterbo et al, Tetrahedron Letters 48, 4617 (1971). Other resolving agents such as (+) camphor-10-sulfonic acid may also be employed. Individual optical isomers of compounds wherein $R_2$ and $R_1$ are other than H and OH respectively may be obtained as described herein for the racemate only starting with the resolved amino acid.

The compounds of general Formula II wherein $R_2$ is hydrogen are prepared by coupling 7-aminocephalosporanic acid or a derivative thereof having the formula

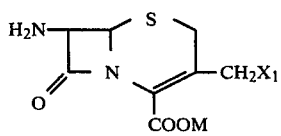

Formula V wherein $X_1$ and M have the meaning defined in general Formula II with an acid of the following Formula VII or a functional derivative thereof, such as, the acid chloride or an acid anhydride

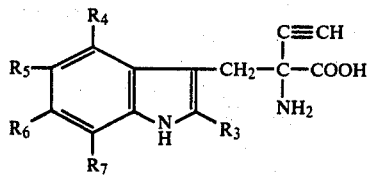

Formula VI wherein $R_3$ to $R_7$ have the meanings defined in Formula I and the amino groups are protected by suitable blocking groups, for example, an acid salt, such as hydrochloride salt, an acyl group, or tert-butoxycarbonyl which groups are removed after the coupling reaction by acid hydrolysis.

The coupling reaction is generally carried out in a solvent, such as, ethyl acetate, dioxane, chloroform, or tetrahydrofuran in the presence of a base, such as alkaline bicarbonate. The temperature of the reaction may vary from −10° C. to 100° C., and the reaction time may vary from about ½ hour to 10 hours. The cephalosporin products are isolated by conventional means.

The compounds of general Formula II wherein $R_2$ is other than hydrogen are prepared from the corresponding derivative wherein $R_2$ is hydrogen by the procedures set forth hereinabove for the compounds of general Formula I wherein $R_2$ is other than hydrogen, that is, when $R_2$ is alkylcarbonyl, alkoxycarbonyl or

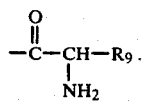

The following examples further illustrate the invention.

EXAMPLE 1

2-Acetylene-2-amino-4-(1,3-dioxolan-2-yl)butyric acid

A solution of 9.8 g (0.046 mole) of 3-trimethylsilyl-prop-2-ynyl-1-iminobenzyl in 200 ml of tetrahydrofuran is treated at −78° C. with 24 ml of a 1.95 M solution of n-butyllithium after which 9.0 g (0.043 mole) of 2-(2-bromoethyl)-1,3-dioxolane is added. The mixture is maintained at −30° C. for 3 hours then water was added and 1-trimethylsilyl-3-iminobenzyl-6-ethylenedioxyhex-1-yne is isolated by ether extraction.

A solution of 6.9 g (0.02 mole) of the above-obtained hexyne derivative in 100 ml of tetrahydrofuran at −78° C. is treated with 10 ml of a 2 M solution of n-bytyllithium after which 1.9 g (0.01 mole) of methyl chloroformate in 5 ml of tetrahydrofuran is added. After 15 minutes the reaction mixture is quenched with brine to give crude 1-trimethylsilyl-3-carbomethoxy-3-iminobenzyl-6-ethylenedioxyhex-1-yne isolated by ether extraction.

A solution of 7.0 g of the crude 1-trimethylsilyl-3-carbomethoxy-3-iminobenzyl-6-ethylenedioxyhex-1-yne in 100 ml of petroleum ether (B.P. 30°–60°) is treated with 2.1 g (0.02 mole) of phenylhydrazine for 4 hours at 25° C. The precipitate is filtered off, the petroleum ether is evaporated, and the residue, taken up in 50 ml of ethanol and 50 ml of water, is treated with 3.3 g (0.06 mole) of potassium hydroxide for 1 hour at 25° C. The ethanol is evaporated, and the aqueous residue is washed well with methylene chloride then carefully neutralized with 1 N HCl. The resulting precipitate is collected and recrystallized from ethanol to give 2-acetylene-2-amino-4-(1,3-dioxolan-2-yl)butyric acid.

When in the procedure of Example 1 an appropriate amount of 2-(2-bromoethyl)-2-methyl-1,3-dioxolane is substituted for 2-(2-bromoethyl)-1,3-dioxolane, 2-acetylene-2-amino-4-(2-methyl-1,3-dioxolan-2-yl)butyric acid is obtained.

EXAMPLE 2

2-Amino-4-(1,3-dioxolan-2-yl)-2-vinylbutyric acid

To 2 g of 2-acetylene-2-amino-4-(1,3-dioxolan-2-yl)butyric acid in 50 ml of liquid ammonia at −30° C. containing 1 g of ammonium sulfate is added lithium metal until the blue color persists for 15 minutes after which solid ammonium chloride is added, and the ammonia allowed to evaporate. The residue is dissolved in water and chromatographed on an Amberlite 120 H+ resin. Elution with 1 M ammonium hydroxide given 2-amino-4-(1,3-dioxolan-2-yl)-2-vinylbutyric acid.

When in the procedure of Example 2 an appropriate amount of 2-acetylene-2-amino-4-(2-methyl-1,3-dioxolan-2-yl)butyric acid is substituted for 2-acetylene-2-amino-4-(1,3-dioxolan-2-yl)butyric acid, 2-amino-4-(2-methyl-1,3-dioxolan-2-yl)-2-vinylbutyric acid is obtained.

EXAMPLE 3

2-Amino-3-[3-(5-hydroxy)indolyl]-2-vinylpropionic acid (A) To 1.23 g (0.005 mole) of p-benzyloxyphenylhydrazine hydrochloride in 200 ml of ethanol and 28 ml of 5% HCl is added slowly 0.9 g (0.005 mole) of 2-amino-4-(1,3-dioxolan-2-yl)-2-vinylbutyric acid in 10 ml of water. The mixture is maintained at 90° C. for 4 hours then concentrated to dryness. The residue is dissolved in water, and the solution is adjusted to a pH of 6. The solution is applied to a column of Amberlite resin 120 H+ and elution with 1 M ammonium hydroxide gives 2-amino-3-[3-(5-benzyloxy)indolyl]-2-vinylpropionic acid which is recrystallized from water.

(B) To 600 mg (1.8 mM) of 2-amino-3-[3-(5-benzyloxy)indolyl]-2-vinylpropionic acid in 100 ml of ammonia was added 100 mg of lithium amide. Lithium metal is added until the blue color persists, then ammonium chloride is added until the mixture becomes colorless, and the ammonia is allowed to evaporate. The residue is taken up in water and washed with methylene chloride. The aqueous phase is adjusted to a pH of 6 and applied to an Amberlite resin 120 H+. Elution with 1 M ammonium hydroxide gives the product which is recrystallized from ethanol/water to give 2-amino-3-[3-(5-hydroxy)indolyl]-2-vinylpropionic acid.

When in the procedure of Example 3 an appropriate amount of 2-amino-4-(2-methyl-1,3-dioxolan-2-yl)-2-vinylbutyric acid is substituted for 2-amino-4-(1,3-dioxolan-2-yl)-2-vinylbutyric acid, 2-amino-3-[3-(5-hydroxy-3-methyl)indolyl]-2-vinylpropionic acid is obtained.

EXAMPLE 4

2-(2-Aminopropionamide)-3-[3-(5-hydroxy)indolyl]-2-vinylpropionic acid

A solution of 260 mg (1 mM) of methyl 2-amino-3-[3-(5-hydroxy)indolyl]-2-vinylpropionate, prepared from the compound of Example 3, in 4 ml of methylene chloride is treated with N-carbobenzoxyalanine (220 mg, 1 mM) and N,N'-dicyclohexyl carbodiimide (206 mg, 1 mM) overnight at 25° C. The mixture is then cooled to 0° C. and the precipitated dicyclohexyl urea filtered off. The filtrate is diluted with methylene chloride, washed with water, bicarbonate solution, then dried and concentrated. The residue is treated with 5 ml of a 40% (w/w) solution of hydrogen bromide in dioxane for 30 minutes at 25° C., then ether added and the precipitate collected, which is treated with 1 N sodium hydroxide (10 ml) overnight at 25° C. The pH of the solution is adjusted to neutral and the product isolated from an Amberlite 120 H+ resin by elution with ammonia (1 M) to afford 2-(2-aminopropionamide)-3-[3-(5-hydroxy)indolyl]-2-vinylpropionic acid.

EXAMPLE 5

2-(1-Oxoethylamino)-3-[3-(5-hydroxy)indolyl]-2-vinylpropionic acid

2-Amino-3-[3-(5-hydroxy)indolyl]-2-vinylpropionic acid (490 mg, 2 mM) is dissolved in 1 N sodium hydroxide solution (4 ml, 4 mM) and cooled to 0° C. Acetic anhydride (1.02 g, 10 mM) is added slowly maintaining the temperature at about 1° C. afterwhich the solution is allowed to warm to 25° C. The solution is stirred at 25° C. for 4 hours, then 1 N sulfuric acid (4 ml, 4 mM) is added. The solution is cooled to 0° C. and maintained at that temperature for about 12 hours. The resultant precipitate of 2-(1-oxoethylamino)-3-[3-(5-hydroxy)indolyl]-2-vinylpropionic acid is filtered off.

When in the procedure of Example 5 an appropriate amount of benzyl chloroformate is substituted for acetic anhydride, 2-(benzyloxycarbonylamino)-3-[3-(5-hydroxy)indolyl]-2-vinylpropionic acid is obtained.

EXAMPLE 6

2-(1-Oxoethylamino)-3-[3-(5-propionyloxy)indolyl]-2-vinylpropionic acid 2-(1-Oxoethylamino)-3-[3-(5-hydroxy)indolyl]-2-vinylpropionic acid (572 mg, 2 mM) is dissolved in 1 N sodium hydroxide solution (4 ml, 4 mM) and cooled to 0° C. Propionyl chloride (600 mg, 6.5 mM) is added slowly maintaining the temperature around 1° C. after which the solution is allowed to warm to 25° C. After 4 hours at 25° C. the solution is treated with 1 N hydrochloric acid (2 ml, 2 mM), and maintained at 0° C. for about 12 hours. The resultant precipitate of 2-(1-oxoethylamino)-3-[3-(5-propionyloxy)indolyl]-2-vinylpropionic acid is filtered off.

In the same manner, but replacing propionyl chloride with phenylacetyl chloride (1 g, 6.5 mM), 2-(1-oxoethylamino)-3-[3-(5-phenylacetyloxy)indolyl]-2-vinylpropionic acid is obtained.

EXAMPLE 7

2-Amino-3-[3-(5-ethoxy)indolyl]-2-vinylpropionic acid hydrobromide 2-(Benzyloxycarbonylamino)-3-[3-(5-hydroxy)indolyl]-2-vinylpropionic acid (378 mg, 1 mM) in dimethyl formamide (2 ml) is added to a suspension of sodium hydride (from 96 mg of a 50% dispension, 2 mM) in dimethyl formamide (5 ml). To the resulting solution ethyl bromide (110 mg) in dimethyl formamide (0.5 ml) is added. This solution is then heated at 80° C. for 6 hours, then poured into water (50 ml) containing 1 N hydrochloric acid (1 ml). This mixture is extracted well with chloroform. The chloroform solution is washed with water, dried and concentrated. The resulting residue is treated with a 40% (w/w) solution of hydrobromic acid in dioxane (3 ml) for 30 minutes at 25° C. after which ether is added and the precipitated 2-amino-3-[3-(5-ethoxy)indolyl]-2-vinylpropionic acid hydrobromide collected.

EXAMPLE 8

2-Amino-3-[3-(5-acetyloxy)indolyl]-2-vinylpropionic acid 2-(Benzyloxycarbonylamino)-3-[3-(5-hydroxy)indolyl]-2-vinylpropionic acid (378 mg, 1 mM) in triethylamine (5 ml) is treated with acetyl chloride (300 ml, 4 mM), and the mixture is stirred overnight at 25° C. The triethylamine is evaporated off and the residue treated with 3 N hydrochloric acid (20 ml) and extracted with ether. The ether solution is washed with water, 1 N hydrochloric acid, water, then dried and concentrated to afford 2-acetylene-2-(benzyloxycarbonylamino)-3-[3-(5-acetyloxy)indolyl]-propionic acid. The propionic acid derivative is treated with 3 ml of a 40% (w/w) solution of hydrogen bromide in dioxane for 30 minutes at 25° C., then diluted with ether and the precipitated 2-amino-3-[3-(5-acetyloxy)indolyl]-2-vinylpropionic acid hydrobromide filtered off.

EXAMPLE 9

2-[2-Amino-3-(5-hydroxyindol-3-yl)-1-oxo-2-vinylpropylamino]-propionic acid 2-(Benzyloxycarbonylamino)-3-[3-(5-acetyloxy)indolyl]-2-vinylpropionic acid (804 mg, 2 mM) prepared from the compound of Example 8 and benzyl chloroformate in methylene chloride (10 ml) is treated with triethylamine (202 mg, 2 mM) followed by ethyl chloroformate (216 mg, 2 mM) in methylene chloride (10 ml). After one hour alanine methyl ester (206 mg, 2 mM) is methylene chloride (5 ml) is added. The solution is kept at 25° C. for about 12 hours, washed with water, then evaporated to dryness. The residue is treated with 5 ml of a 40% (w/w) solution of hydrogen bromide in dioxane for 30 minutes at 25° C. Ether is then added and the precipitated N-(2-propionic acid methyl ester)-2-amino-3-[3-(5-acetyloxy)indolyl]-2-vinylpropionyl carboxamide hydrobromide filtered off. The carboxamide hydrobromide derivative is treated with 1 N sodium hydroxide solution (15 ml) at 25° C. for about 12 hours after which the pH of the solution is adjusted to 6.5 and the solution added to Amberlite 120 H+ resin. Elution with 1 M ammonium hydroxide afforded 2-[2-amino-3-(5-hydroxyindol-3-yl)-1-oxo-2-vinylpropylamino]propionic acid.

EXAMPLE 10

N-n-Propyl 2-amino-3-[3-(5-hydroxy)indolyl]-2-vinylpropionamide 2-(Benzyloxycarbonylamino)-3-[3-(5-acetyloxy)indolyl]propionic acid (840 mg, 2 mM) in methylene chloride (10 ml) is treated with thionyl chloride (240 mg, 2 mM) at 25° C. for one hour. n-Propylamine (708 mg, 6 mM) is then added and the solution is stirred for one hour at 25° C. then washed with water, dried and evaporated. The residue is treated with a 40% (w/w) solution of hydrogen bromide in dioxane (5 ml) at 25° C. for 30 minutes, then ether is added and the precipitated N-n-propyl-2-acetylene-2-amino-3-[3-(5-acetyloxy)indolyl]propionamide hydrobromide is filtered off. The propionamide derivative is treated with 1 N sodium hydroxide solution (5 ml, 5 mM) for 2 hours at 60° C. On cooling, 1 N hydrochloric acid (3 ml) is added, the solution concentrated to approximately 3 ml, cooled to 0° C. and the precipitated N-n-propyl 2-amino-3-[3-(5-hydroxy)indolyl]-2-vinylpropionamide is filtered off.

EXAMPLE 11

Methyl 2-amino-3-[3-(5-hydroxy)indolyl]-2-vinylpropionate hydrochloride

2-Amino-3-[3-(5-hydroxy)indolyl]-2-vinylpropionic acid (488 mg, 2 mM) is suspended in methanol (30 ml) which had previously been saturated with dry hydrogen chloride. The mixture is stirred at 25° C. for 24 hours, then the solvent removed under reduced pressure. The residue is recrystallized from methanol-ether to afford methyl 2-amino-3-[3-(5-hydroxy)indolyl]-2-vinylpropionate hydrochloride.

The following illustrates the use of the compounds of general Formula I wherein $R_1$ is hydroxy in the preparation of the useful cephalosporin derivatives of general Formula II.

EXAMPLE 12

7-[[2-amino-3-[3-(5-hydroxy)indolyl]-2-vinylpropionyl]amino]-3-acetoxymethyl-8-oxo-5-thia-1-azabicyclo[4.2.0]oct-2-ene-2-carboxylic acid A mixture of 1 g of 3-acetyloxymethyl-7-amino-8-oxo-5-thia-1-azabicyclo[4.2.0]oct-2-ene-2-carboxylic acid and 1 g of 2-acetylene-2-amino-3-[3-(5-hydroxy)indolyl]propionic acid chloride wherein the free amino groups are protected with tert-butoxycarbonyl in 50 ml of ethyl acetate is refluxed for 2 hours after which the solvent is removed leaving a residue which is chromatographed on silica gel using benzene-acetone as the eluant to give 7-[[2-amino-3-[3-(5-hydroxy)indolyl]-2-vinylpropionyl]-amino]-3-acetoxymethyl-8-oxo-5-thia-1-azabicyclo[4.2.0]oct-2-ene-2-carboxylic acid wherein the amino groups are protected with tert-butoxycarbonyl. The protected cephalosporin compound is treated with trifluoroacetic acid for ½ hour at 25° C. under nitrogen atmosphere then diluted with ether until precipitation stops and filtered to give the di-trifluoroacetic acid salt of the title cephalosporin which can be converted to the free base by use of ion exchange resin.

The following examples are illustrative of pharmaceutical preparations of compounds of general Formula I.

EXAMPLE 13

An illustrative composition for hard gelatin capsules is as follows:

| | | |
|---|---|---|
| (a) | 2-amino-3-[3-(5-hydroxy)-indolyl]-2-vinylpropionic acid | 10 mg |
| (b) | talc | 5 mg |
| (c) | lactose | 100 mg |

The formulation is prepared by passing the dry powders of (a) and (b) through a fine mesh screen and mixing them well. The powder is then filled into hard gelatin capsules at a net fill of 115 mg per capsule.

EXAMPLE 14

An illustrative composition for tablets is as follows:

| | | |
|---|---|---|
| (a) | 2-amino-3-(3-indolyl)-2-vinylpropionic acid | 5 mg |
| (b) | starch | 43 mg |
| (c) | lactose | 60 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 15

An illustrative composition for an aerosol solution is the following:

| | | Weight per cent |
|---|---|---|
| (a) | 2-amino-2-[3-(5-hydroxy)-indolyl]-2-vinylpropionic acid | 5 |
| (b) | ethanol | 35 |
| (c) | dichlorodifluoromethane | 60 |

The materials (a), (b) and (c) are packaged in 15 ml stainless steel containers equipped with a metering valve designed to meter 0.2 grams per dose, an equivalent of 40 mg of novel compound (a).

EXAMPLE 16

An illustrative composition for an injectable suspension is the following 1 ml ampul for an intramuscular injection.

| | | Weight per cent |
|---|---|---|
| (a) | 2-amino-3-[3-(5-(1-oxoethoxy))indolyl]-2-vinylpropionic acid | 1.0 |
| (b) | polyvinylpyrrolidone | 0.5 |
| (c) | lecithin | 0.25 |
| (d) | water for injection to make | 100.0 |

The materials (a)-(d) are mixed, homogenized, and filled into 1 ml ampuls which are sealed and autoclaved 20 minutes at 121° C. Each ampul contains 10 mg per ml of novel compound (a).

EXAMPLE 17

An illustrative composition for an aerosol suspension is the following:

| | | Weight per cent |
|---|---|---|
| (a) | methyl 2-amino-3-[3-(5-hydroxy)-indolyl]-2-vinylpropionic acid (particle size < 10μ) | 20.0 |
| (b) | sorbitan trioleate | 0.5 |
| (c) | dichlorodifluoromethane | 39.75 |
| (d) | dichlorodifluoroethane | 39.75 |

The materials (a)-(d) are packaged in 15 ml stainless steel containers equipped with a metering valve designed to meter 50 mg per dose, an equivalent of 10 mg of novel compound (a).

EXAMPLE 18

2-(1-Oxoethylamino)-3-[3-(6-hydroxy)indolyl]-2-vinylpropionate

A mixture of 1.28 g (10 mM) of 3-methoxyphenylhydrazine and 2.1 g (10 mM) of methyl 2-(1-oxoethylamino)-5-oxo-2-vinylpentanoate is heated under reflux in 20 ml of benzene with azeotropic removal of water. The benzene is removed and the residue treated with 20 ml of 6 N HCl and 20 ml of ethanol. The mixture is heated under reflux for 1 hour, diluted with 200 ml of water and extracted with dichloromethane. The residue after removal of the solvent is treated with 30 ml of methanol saturated with dry hydrogen chloride overnight at 25° C. then evaporated leaving a residue which is chromatographed on florisil eluting with 3% methanol-chloroform to give first methyl 2-(1-oxoethylamino)-3-[3-(4-methoxy)indolyl]-2-vinylpropionate (100 mg) and second 2-(1-oxoethylamino)-3-[3-(6-methoxy)indolyl]-2-vinylpropionate (550 mg). The 6-methoxy derivative (314 mg, 1 mM) in 10 ml of dichloromethane is treated with 300 mg of boron tribromide overnight at 25° C. after which 10 ml of methanol is added and the mixture evaporated to dryness. The residue is crystallized from ethyl acetate to give 2-(1-oxoethylamino)-3-[3-(6-hydroxy)indolyl]-2-vinylpropionate.

EXAMPLE 19

Methyl 2-(1-oxoethylamino)-3-[3-(4-methoxy)indolyl]2-vinylpropionate and methyl 2-(1-oxoethylamino)-3-[3-(6-methoxy)indolyl]-2-vinylpropionate To 1.38 g (10 mM) of m-methoxyphenylhydrazine and 28 ml of 10% HCl is added slowly 1.8 g (10 mM) of 2-amino-4-(1,3-dioxolan-2-yl)-2-vinylbutyric acid in 10 ml of water. The mixture is maintained at 90° C. for 4 hours then concentrated to dryness leaving a residue which is dissolved in 30 ml of methanol saturated with dry hydrogen chloride. After stirring overnight at 25° C. the solvent is evaporated and the residue, suspended in 20 ml of dichloromethane, is treated with 780 mg of acetyl chloride and 300 mg of triethylamine overnight at 25° C. The solution is then washed with water, dried over magnesium sulfate and evaporated leaving a residue which is chromatographed on florisil. Elution with 3% methanol chloroform gives first methyl 2-(1-oxoethylamino)-3-[3-(4-methoxy)indolyl]-2-vinylpropionate and methyl 2-(1-oxoethylamino)-3-[3-(6-methoxy)indolyl]-2-vinylpropionate.

We claim:

1. A compound of the formula

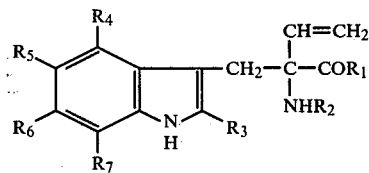

wherein $R_1$ is hydroxy, a straight or branched alkoxy group of from 1 to 8 carbon atoms, —NYY' wherein each of Y and Y' is hydrogen or a straight or branched lower alkyl of from 1 to 4 carbon atoms, or

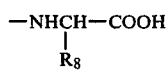

wherein $R_8$ is hydrogen, a straight or branched lower alkyl group of from 1 to 4 carbon atoms, benzyl or p-hydroxybenzyl; $R_2$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

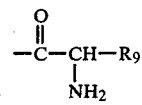

wherein $R_9$ is hydrogen, a straight or branched lower alkyl group of from 1 to 4 carbon atoms, benzyl or p-hydroxybenzyl; $R_3$ is hydrogen or methyl; $R_4$, $R_5$, $R_6$ and $R_7$ have the meanings defined in Table I wherein $R_{10}$ is hydrogen, a straight or branched alkyl group of from 1 to 8 carbon atoms, alkylcarbonyl wherein the alkyl moiety has from 1 to 6 carbon atoms and is straight or branched, benzoyl or phenylalkylenecarbonyl wherein the alkylene moiety has from 1 to 6 carbon atoms and is straight or branched, and halo is chlorine, fluorine, bromine or iodine;

TABLE 1

| $R_4$ | $R_5$ | $R_6$ | $R_7$ |
|---|---|---|---|
| H | H | H | H |
| H | $OR_{10}$ | $OR_{10}$ | H |
| $OR_{10}$ | H | H | H |
| H | $OR_{10}$ | H | H |
| $OR_{10}$ | H | $OR_{10}$ | H |
| H | H | $OR_{10}$ | H |
| $OR_{10}$ | $OR_{10}$ | H | H |
| $CF_3$ | H | H | H |
| H | H | $CF_3$ | H |
| H | halo | H | H |
| H | H | halo | H |
| H | halo | halo | H |
| halo | H | H | $CH_3$ |
| $OR_{10}$ | H | H | $CH_3$ |
| H | $OR_{10}$ | H | $CH_3$ |
| H | H | $OR_{10}$ | $CH_3$ |
| H | H | H | halo |
| H | halo | H | halo |
| H | H | halo | halo |
| halo | H | H | halo |
| H | H | $OR_{10}$ | halo |
| H | $OR_{10}$ | H | halo |
| $OR_{10}$ | H | H | halo |
| H | H | H | $CF_3$ |
| H | $OR_{10}$ | H | $CF_3$ |
| H | H | halo | $OR_{10}$ |
| H | $OR_{10}$ | H | $OR_{10}$ |
| H | halo | H | OR |
| $OR_{10}$ | H | H | $OR_{10}$ |
| halo | H | H | $OR_{10}$ | or a pharmaceutically acceptable salt and individual optical isomers thereof.

2. A compound of claim 1 wherein $R_2$ is hydrogen or alkylcarbonyl wherein the alkyl moiety has from 1 to 4 carbon atoms and is straight or branched.

3. A compound of claim 1 wherein $R_1$ is hydroxy or a straight or branched alkoxy group of from 1 to 8 carbon atoms.

4. A compound of claim 1 wherein each of $R_4$, $R_5$, $R_6$ and $R_7$ is hydrogen or $OR_{10}$ wherein $R_{10}$ is hydrogen.

5. A compound of claim 4 wherein $R_1$ is hydroxy and $R_2$ is hydrogen.

6. A compound of claim 4 wherein $R_5$ is hydrogen or $OR_{10}$ wherein $R_{10}$ is hydrogen.

7. A compound of claim 5 which is 2-amino-3-(3-indolyl)-2-vinylpropionic acid or a pharmaceutically acceptable salt thereof.

8. A compound of claim 5 which is 2-amino-3-[3-(5-hydroxy)indolyl]-2-vinylpropionic acid or a pharmaceutically acceptable salt thereof.

* * * * *